United States Patent
Hedin et al.

[19]

[11] Patent Number: 5,822,069
[45] Date of Patent: Oct. 13, 1998

[54] APPARATUS AND METHOD FOR PERFORMING FLUOROMETRIC MEASUREMENT

[75] Inventors: Björn Hedin; Henry Andersson, both of Upsala; Lars Eriksson, Haninge; Torbjörn Bladh, Storvreta, all of Sweden

[73] Assignee: Pharmacia & Upjohn Diagnostics AB, Stockholm, Sweden

[21] Appl. No.: 894,611

[22] PCT Filed: Feb. 16, 1996

[86] PCT No.: PCT/SE96/00205

§ 371 Date: Dec. 8, 1997

§ 102(e) Date: Dec. 8, 1997

[87] PCT Pub. No.: WO96/30744

PCT Pub. Date: Oct. 3, 1996

[30] Foreign Application Priority Data

Mar. 24, 1995 [SE] Sweden .................................. 9501069

[51] Int. Cl.[6] .................................................. G01N 21/64
[52] U.S. Cl. .................... 356/417; 250/458.1; 250/461.1
[58] Field of Search .................................... 356/417, 317, 356/318; 250/458.1, 459.1, 461.1, 461.2

[56] References Cited

U.S. PATENT DOCUMENTS 4,548,498 10/1985 Folestad et al. .
4,861,163 8/1989 Bach ........................................ 356/417
5,615,008 3/1997 Stachelek ................................ 356/318

FOREIGN PATENT DOCUMENTS 0488152 6/1992 European Pat. Off. .
0521636 1/1993 European Pat. Off. .

Primary Examiner—F. L. Evans
Attorney, Agent, or Firm—Dinsmore & Shohl LLP

[57] ABSTRACT

This invention relates to an apparatus and a method for performing fluorometric measurements, and particularly to a fully automated apparatus for measuring the fluorescence of a fluorescent tag contained in a test sample for allergy assays. Said apparatus comprising, an excitation radiation source (6) including an incandescent filament (30) cooperating with, an optical unit (4) for providing light of an appropriate wavelength for excitation of the fluorescent tag contained within the test sample, and for collecting the emitted fluorescent radiation without disturbances from the excited wavelength, an electronic unit (2) for controlling the intensity of the incandescent filament (30) of the excitation radiations source (6) and evaluating the emitted fluorescent radiation, said optical unit (4) comprising an L-shaped light channel (34), and a capillary tube (8) movably provided at the centre of the intersection between the two legs of the L-shaped light channel (34) and aligned with the incandescent filament (30), said capillary tube (8) being moveable between two positions and being repeatedly, between each measurement, suppliable with a new test sample.

19 Claims, 4 Drawing Sheets

APPARATUS AND METHOD FOR PERFORMING FLUOROMETRIC MEASUREMENT

FIELD OF THE INVENTION

This invention relates to an apparatus and a method for performing fluorometric measurements, and particularly to a fully automated apparatus for measuring the fluorescence of a fluorescent tag contained in a test sample for allergy assays and which repeatedly measures the fluorescence of different samples under the same conditions and with the same high accuracy.

BACKGROUND OF THE INVENTION

Today allergy assays are made more and more automatically without involvement of any human personnel between different steps of the process. One step in performing an allergy test is to measure the fluorescence of a test sample. This can today be made fully automatically, but there are still many deficiencies.

One common fluorometer for measuring the fluorescence in a sample uses a tray with a plurality of depressions which contain the samples. The tray is inserted into a fluorometer which scans over the samples in order to measure the fluorescence of each sample. One drawback to this fluorometer is that the depressions differ in size and exhibit irregularities which affect the beam path and it is therefore difficult to obtain measurements with high accuracy, since the calibration of the fluorometer has to be carried out in regard to these irregularities and the average size of the depressions.

U.S. Pat. No. 4,447,546 discloses a fluorescent immunoassay apparatus and a method for performing assays, wherein a fluorescent tag capable of emitting fluorescent radiation when excited by more energetic radiation is incorporated into a constituent of an antigen-antibody complex. The apparatus consists of capillary tubing, a fibre and a fluorometer. The fibre has a coating for forming said antigen-antibody complex. The sample to be assayed is drawn into the tubing by capillary action. The depth of the test sample layer on the fibre depends on the incubation time. After the incubation time the fluorometric measurement is then made by using total reflection fluorescence techniques.

The apparatus described in the above U.S. Patent does not work fully automatically, since a person has to bring the optical fibre in the capillary tube to the fluorometer. This could be a source of inaccuracy, since it is not certain that the capillary tube containing the fibre always is lined up in the same way at the fluorometer. A further drawback to this apparatus is that the fibre and capillary tubing are of a disposable type, i.e. a new set of fibre and tubing is used for each new measurement. Thus, this apparatus and method is not directed towards a fully automated system for repeatedly measuring the fluorescence in different samples.

U.S. Pat. No. 4,454,235 discloses an apparatus and a method for transferring fluids in a multi-liquid reagent protocol. Fluid transfer is effected through a capillary tube having a calibrated bore. Once filled the capillary tube holder is then inserted into a second cuvette. The content of the capillary tube is discharged in the liquid of the second cuvette. Assay results are then obtained by inserting the second cuvette and the reaction product of the second regent within a fluorometer.

This apparatus and method also requires manual handling between different steps of the assay. The main object in this patent is to transfer an exact amount of fluid between two cuvettes and the description does therefore not address the problem how to automate the process in order to speed up the time required for performing an assay. Manual handling of course also affects the accuracy of the assay result since the measurements will be made under different conditions.

U.S. Pat. No. 4,548,498 discloses a method and a device for laser induced fluorescence detection in liquid chromatography, in which a beam of light is directed from a laser source towards a liquid flowing in a chosen flow direction for the detection of one or several substances. This invention is directed towards determining which substances are being present in a flowing liquid and does not focus on the problem to automatically measure the fluorescence in one sample at a time which is the case with allergy assays.

There are numerous other patents that focus on fluorescence measurements, such as U.S. Pat. No. 4,978,503 which discloses a sample collecting and testing device for use in fluoroimmunoassay and U.S. Pat. No. 5,221,958 which discloses a reflection fluorometer.

However all patents cited above are either directed towards the fluorometer itself or describe an apparatus for manually assaying test samples. Therefore a need exists for an apparatus and a method for performing fully automated fluorometric measurements, particularly allergy assays, in which the fluorescence of different samples are repeatedly measured under the same condition and with the same high accuracy.

SUMMARY OF THE INVENTION

The object of the present invention is therefore to provide an apparatus and a method for performing fluorometric measurements without personnel involvement and with a high accuracy by maintaining same the measurement conditions for all samples being measured.

The object is solved with an apparatus comprising an excitation radiation source including a incandescent filament, cooperating with an optical housing for providing light of an appropriate wavelength for excitation of the fluorescent tag contained within the test sample and for collecting the emitted fluorescent radiation without disturbances from the excited wavelength, said optical housing comprising an L-shaped light channel, an electronic unit controlling the intensity of the excitation radiation source and evaluating the emitting fluorescent radiation, and a capillary tube movably provided at the centre of the intersection between the two legs of the L-shaped light channel and aligned with the incandescent filament, said capillary tube being moveable between two position and being repeatedly, between each measurement, suppliable with a new test sample.

An advantage with the present invention is the ability to perform automatic fluorescent measurements under exactly the same conditions. This is achieved by that the capillary tube containing the test sample with fluorescent tag is one and the same for each measurement, as long as it does not break. By means of a step motor, a threaded shaft, securing means, a guiding tube, a guiding plate and a guiding track the capillary tube is moveable between two positions, namely a lower position at which the fluorometric measurement and a cleaning procedure is performed and an upper position at which a new test sample is rotated in place directly underneath the capillary tube.

Other features of the apparatus according to the present invention are defined in the dependent claims 2 to 17 and the method according to the present invention is defined in claim 18.

BRIEF DESCRIPTION OF THE DRAWINGS

The present invention and many of the advantages of the present invention will be readily appreciated as the same become better understood by reference to the following description when considered in connection with the accompanying drawings, in which like reference numerals designate like parts throughout the figures thereof and wherein.

DETAILED DESCRIPTION OF THE PREFERRED EMBODIMENT

The main features of the apparatus according to the present invention will first be described referring to FIG. 1. Thereafter the lamp housing 6, and the optical housing 4 will be described referring to FIG. 2. The electronic unit 2 will then be described in conjunction with FIG. 3. Finally the method according to the present invention will be described with reference to the flow chart in FIG. 4.

Figure 1:
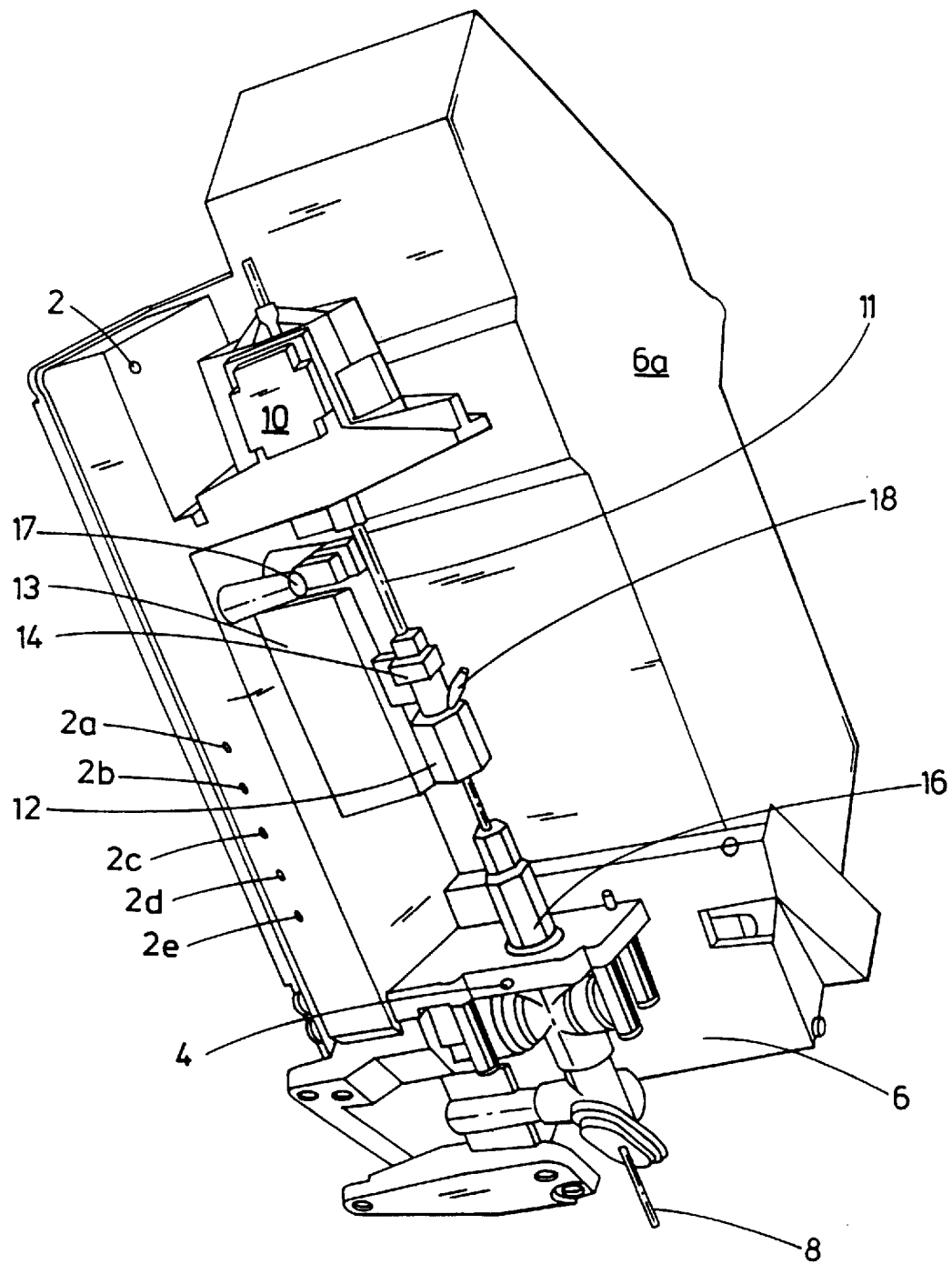
FIG. 1 is an overall perspective view of an apparatus performing fluorometric measurements according to the present invention.

FIG. 1 is an overall perspective view of an apparatus performing fluorometric measurements according to the present invention. The apparatus in FIG. 1 comprises an electronic unit 2, an optical housing 4, a lamp housing 6, 6a, a capillary tube 8, a step motor 10, a threaded shaft 11, securing means 12, a guiding track 13, a guiding plate 14, a guiding tube 16, an optical sensor 17 and a nipple 18.

The apparatus in FIG. 1 is consists of two larger blocks, namely the lamp housing 6, 6a and the electronic unit 2, which are arranged such that they form a 90 degree angle between each other. The lamp housing 6, 6a actually consists of two parts, the actual lamp housing 6 and the cooling channel 6a. The cooling channel 6a is used to remove excess heat from the lamp housing 6 and comprises a fan and cooling flanges, neither of which are shown in FIG. 1. The electronic unit 2 has the shape of a rectangular box and is provided with five holes 2a–2e, through which different setting screws may be accessed.

At the top of the space between the electronic unit 2 and the lamp housing 6, 6a the step motor 10 is provided. The threaded shaft 11 is provided at the lower end of the step motor 10 and extends towards the bottom of said space between the electronic unit 2 and the lamp housing 6, 6a and runs parallel thereto. The threaded shaft 11 is provided with a guiding plate 14 which runs in a guiding track 13 provided on top of the electronic unit 2 to ensure that the threaded shaft 11 and the capillary tube 8, to be described below, always are kept in parallel with the electronic unit 2 and the lamp housing 6, 6a.

At the end of the threaded shaft 11 securing means 12 is provided, to which the capillary tube 8 is fixedly secured. The securing means 12 is further provided with two nipples 18 of which only one can be seen in FIG. 1. At those nipples two hoses (not shown) are connected. The first one leads to a suction device used to draw the test sample into the capillary tube 8 prior to the measurement and to empty the capillary tube 8 after the measurement has been performed. The second hose leads to a water supply and is used to flush and clean the capillary tube 8 after each measurement. The capillary tube 8 extends in the same direction as the threaded shaft 11 and passes through a guiding tube 16 and the optical housing 4 before it reaches the bottom of the space between the electronic unit 2 and the lamp housing 6, 6a. The optical housing 4 is arranged between the electronic unit 2 and the lamp housing 6, 6a and its top surface is perpendicular to both of those.

The apparatus in FIG. 1 is further provided with the optical sensor 17 at the upper end of the guiding track 13. This optical sensor 17 is used to determine if the guiding plate 14 and thereby the capillary tube 8 has reached its upper position. The lower position is reached and determined when the guiding plate 14 abuts the securing means 12.

Figure 2:
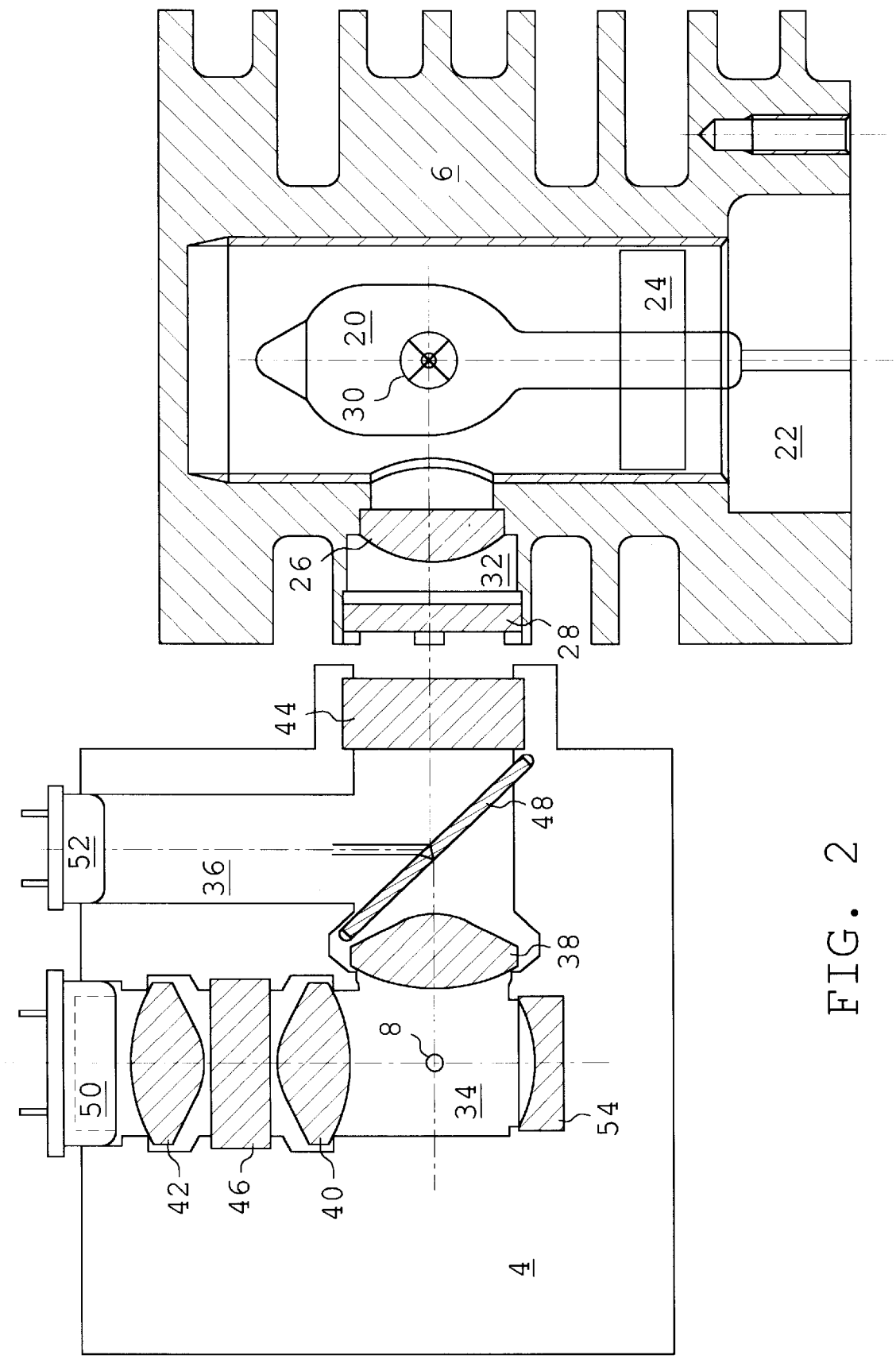
FIG. 2 is a schematic view of the lamp housing and the optical housing in the apparatus according to the present invention.

FIG. 2 shows an enlarged view of the lamp housing 6 and the optical housing 4. The lamp housing 6 comprises a lamp 22, a lamp holder 22, a adjusting element 24, a lens 26, a filter 28, a light channel 32 and also cooling flanges and cooling channels which are not shown in FIG. 2. The latter two are incorporated inside the housing 6a (FIG. 1), as described earlier in conjunction with FIG. 1.

The lamp housing 6 and the optical housing 4 are formed to be mounted closely together. The mounting of these two housings can only be performed one precise way, i.e they will always have the same fixed relation to each other. This is done to ensure that the incandescent filament 30 of the lamp 20 always is aligned with the capillary tube 8 of the optical housing 4. Providing for a fixed relationship between the lamp housing 6 and the optical housing 4 also improves the maintenance routine for the apparatus, since the operator only has to remove the lamp housing 4 incorporating the lamp 20 and replace it with a new one whenever it is needed. Since the lamp housing 4 only fits one way no errors can occur when replacing it. Authorized technicians may then mount a new lamp 20 into the lamp holder 22 of the lamp housing 6 and adjust the lamp 20 by means of the adjusting element 24 so it always will be aligned with the capillary tube 8 of the optical housing 4 when operators substitute an old lamp housing 6 with a new one.

The lamp housing 6 further includes the light channel 32 provided at the one side of the lamp housing 6 which is closest to the optical housing 4. The middle of the light channel 32 corresponds to the incandescent filament 30 of the lamp 20 which is shown with a dotted line in FIG. 2. The light channel 32 incorporates the lens 26 and the filter 28. The lens 26 is the one closest to the lamp 20 and is a condenser lens making the light parallel in the light channel 32 of the lamp housing 6. The filter 28 which is closest to the outlet of the light channel 32 acts as an IR filter, i.e filters the heat in order to prevent the following filter in the optical housing 4 from being damaged.

The light channel 32 of the lamp housing 6 propagates in the light channel 34 of the optical housing 4. In fact these both light channels 32, 34 form one and the same channel, since the lamp housing 6 and the optical housing 4 are mounted closely together as may be clearly seen in FIG. 1. The view in FIG. 2 is thus only a schematic view used to describe the lamp housing 6 and the optical housing 4.

The optical housing 4 comprises two light channels 34 and 36, three lenses 38, 40, 42, two filters 44, 46, a beam divider 48, two diodes 50, 52, and a mirror 54.

The first light channel 34 in the optical housing has the shape of an L. The open end of the bottom leg of the L-shaped light channel 34 begins where the light channel 32 of the lamp housing 6 ends, as previously described. Thus, the light that falls into this opening is the light exiting the light channel 32 and runs in parallel with the sides of said light channel 34 due to the condenser lens 26 and is essentially free from heat due to the IR-filter 28.

The first element in the light channel 34, which receives the light as described above, is an excitation filter 44. This filter 44 filters out the wavelength that will excite the fluorescent tag in the test sample contained within the capillary tube 8. In the preferred embodiment shown in the figures this wavelength is 370 nm. Of course this wavelength may vary depending on the fluorescent tag used in the test sample.

Next element in the L-shaped light channel 34 is a beam divider 48 which divides the parallel light in two separate directions. The first direction, i.e the main direction, is straight ahead towards the test sample and the second direction, which is displaced 90 degrees from the first direction, is directed into the second light channel 36 of the optical housing 4. Thus, the second light channel 36 has a direction that is parallel with the upstanding leg of the L-shaped light channel 34. This second light channel 36 is used to collect reference light which in turn is to be used to control the intensity of the light radiated from the lamp 20, which will be described below in conjunction with FIG. 3 describing the electronic unit 2.

In the preferred embodiment experience has shown that if 90% of the light is directed into the main direction and 10% of the light is directed into the reference direction an optimum relationship will be obtained for the purposes of the present invention. The invention is of course not limited to this and depending on the application of the present invention different ratios may be used to obtain an optimum relationship.

The light entering the second light channel 36 also runs in parallel with the sides of light channel 36 and is not further obstructed before it impinges onto the reference diode 52 at the end of the light channel 36. The reference diode 52 is an ordinary silicon diode, but could of course also be any other suitable means used to measure the intensity of light. The reference diode 52 is connected to the electronic unit 2, which as already mentioned uses the signal from the reference diode 52 to control the intensity of light radiated by the lamp 20.

The main part (90%) of the light that runs straight ahead towards the capillary tube 8 is still parallel with the sides of the light channel 34 after passing the beam divider 48 and passes further trough an aspherical lens 38 before it impinges against the capillary tube 8. The aspherical lens 38 is used to focus the light on the capillary tube 8.

The capillary tube 8 is movably provided at the centre of the intersection between the two legs of the L-shaped light channel 34 and aligned with the incandescent filament of the lamp 20. The capillary tube is moveable up and down between two fixed positions as described above in conjunction with FIG. 1. In the first position, i.e. the measuring position, which is the lower position the capillary tube 8 containing the test sample is in a position which allows the impinging light to excite the fluorescent tag in the sample. The bottom end of the capillary tube 8 is at this position immersed into the test sample liquid. The test sample is contained in a container directly beneath the capillary tube 8. In the second position which is the upper position the capillary tube 8 is not longer immersed into the test sample and the container is clear to rotate one position bringing a new container into place for the next measurement.

After the capillary tube 8 the light channel 34 makes a 90 degree turn. A mirror 54 is provided at the bottom of the upstanding leg of the L-shaped light channel 34. The mirror has a curvature which is adapted for reflecting as much of the emitting light from the fluorescent tag as possible.

In the upstanding leg of the L-shaped light channel 34 a further aspherical lens 40 is provided to make the emitted light from the fluorescent tag run in parallel with the sides of the light channel 34 again. After the aspherical lens 40 an emission filter 46 is provided, which filters out the emitted light and prevents the excited light from passing. The wavelengths that are allowed to pass are centred around 450 nm, which is the wavelength of the light emitted in this embodiment. This wavelength is of course dependent on the fluorescent tag used and the present invention is not limited by the wavelength used in this embodiment of the present invention.

Before the light channel 34 ends at the diode 50 it passes yet another aspherical lens 42 that focuses the light emitted on the diode 50, which is of the same type as the reference diode but larger, i.e a silicon diode. The diode 50 is connected to the electronic unit 2, in which the signal coming from the diode 50 is evaluated and outputted.

Figure 3:
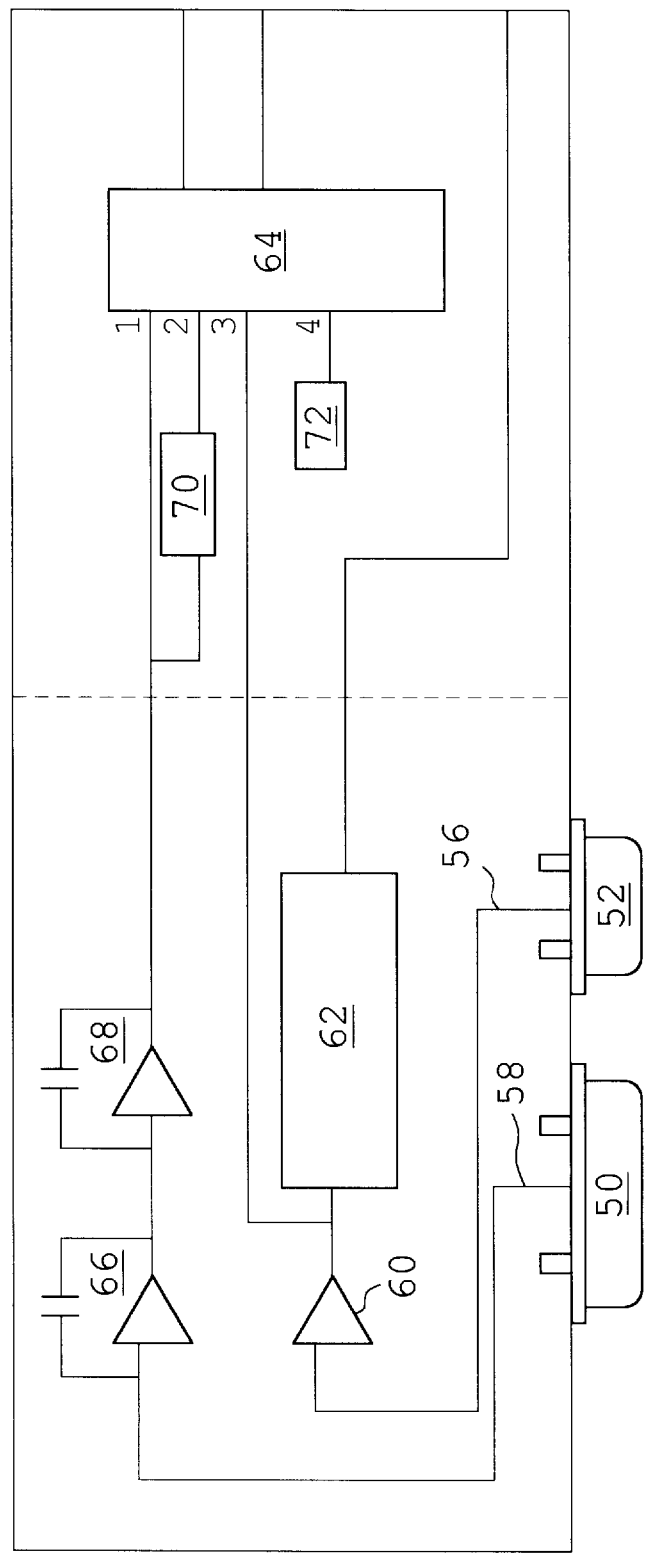
FIG. 3 is a schematic view of the electronic unit of the apparatus according the present invention.

FIG. 3 shows the electronic unit 2 which is used to evaluate and output the values obtained from the light emitted by the fluorescent tag contained in the test sample. The electronic unit 2 according to the present invention is made up of commonly used electronic elements and is as such not a part of the invention.

The electronic unit 2 has two inputs 56, 58, of which the first one is connected to the reference diode 52 and the second one is connected to the measuring diode 50. The first input 56 is connected to an operational amplifier 60 in order to amplify the signal coming from the reference diode 52. The output of the amplifier 60 is connected to a light regulator 62 and to a third input of an analog to digital converter 64 (ADC) which serves as an interface between the analog signals obtained from the diodes and the microcomputer used to evaluate the fluorometric measurement.

The light regulator 62 compares the amplified voltage signal with a set reference voltage within the light regulator 62. The difference therebetween is used to generate a control signal which is applied to the lamp 20 in the lamp housing 6. Thus, the output of the light regulator 62 is connected to the lamp 20. In this fashion the light radiated from the lamp 20 always will have the same intensity and measuring errors connected with varying intensity of light will thus be neglectable.

The second input 58 of the electronic unit 2 is connected to an integrator circuit 66, with an integrating time of approximately 2 seconds. This is done to suppress the noise of the signal coming from the measuring diode 50. The output of the integrator circuit 66 is connected to a track and hold circuit 68 which is used to stabilize the signal before it is applied to the ADC 64. The output of the track and hold circuit 68 is thus connected to a first input of the ADC 64 and to a second input of the ADC 64 via an attenuation circuit 70. The two different inputs of which one is attenuated and the other is unattenuated make it possible to display the same signal on different scales.

The electronic unit 2 further comprises a temperature circuit 72 which is used to obtain a temperature signal. This signal is used to balance the apparatus so it is unsensitive to the ambient temperature. The output of this temperature circuit 72 is connected to a fourth input of the ADC 64.

Thus, the ADC 64 thus has a total of four inputs. The outputs of the ADC 64 also serve as outputs for the electronic unit 2 and are connected to a microcomputer or any other suitable means, such as a computer, display means, etc for evaluating and/or displaying the measured values.

Figure 4:
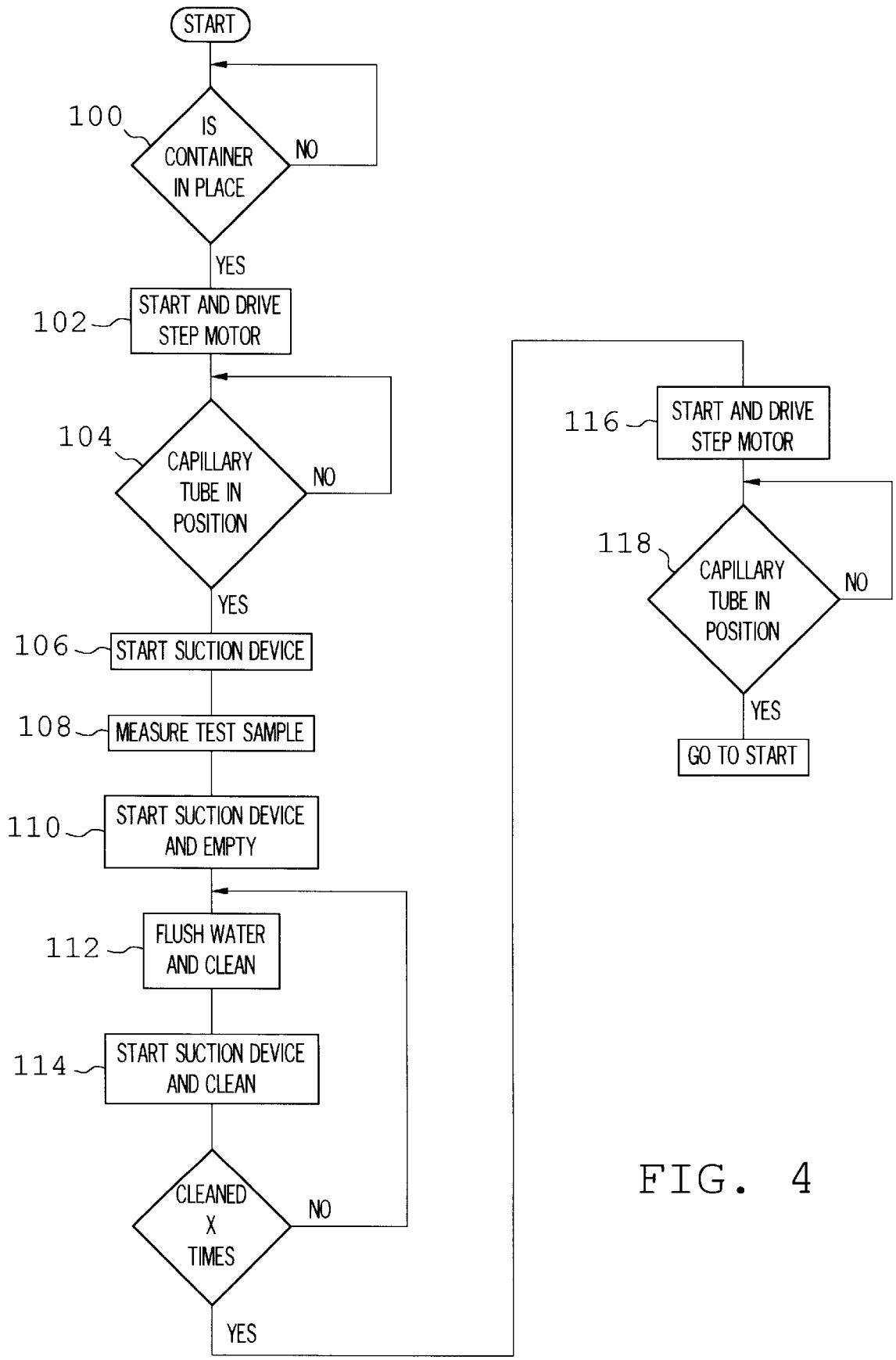
FIG. 4 is a flow chart showing the method according to the present invention.

The four setting screws described above in conjunction with FIG. 1 and which may be accessed through the holes 2a–2e are not shown i FIG. 4 for reasons of simplicity. These setting screws are used in a calibration process in which for example the offset of an operational amplifier may be set. This is assumed to be within the knowledge of those skilled in the art and is therefore not described in any more detail.

FIG. 4 is a flow chart showing the method for measuring the emitting light of a fluorescent tag contained in a test sample according to the present invention. At the time when the fluorometric measurement starts the capillary tube 8 is in its upper position. This permits the first container to be rotated in a position directly underneath the capillary tube 8.

The containers that contain the test sample are not as such a part of the invention, but are still described to get a more complete understanding of the present invention. The containers are provided on a rotating tray or the like and are rotated in position one after another between each measurement.

The first step 100 after activating the apparatus is to determine if the first container is in place. If the answer at step 100 is no the apparatus waits until the answer at step 100 is yes and then proceeds to the next step 102. At this step 102 the step motor 10 starts and drives the capillary tube 8 downwards by means of the threaded shaft 11, the guiding plate 14 and the guiding track 13.

Next step 104 is to determine if the capillary tube has reached its lower position. If the answer at step 104 is no the step motor continues to drive the capillary tube 8 downwards until the guiding plate 14 abuts the securing means 12. At this moment the capillary tube 8 is immersed into the test sample liquid and the answer at step 104 is yes and the next step 106 follows.

At step 106 the suction device is activated and applies a suction force to the test sample liquid through the above mentioned first hose, the nipple 18 and the capillary tube 8. In this manner the capillary tube 8 will be filled with the test sample containing the fluorescent tag. When this step 106 is finished the measurement of the amount of fluorescent tag contained in the test sample begins.

In the measuring step 108 the test sample in the optical housing 4 will receive the excited light and emits light which is collected by the diode 50. After measuring the fluorescence of the test sample the suction device starts once again at step 110 and empties the container and the capillary tube 8 from the test sample and thereafter proceeds to step 112.

At step 112 the second hose will supply water to the capillary tube 8 and the container from a water supply. This step 112 flushes and cleans the capillary tube 8 and the container. Thereafter the suction device starts once again at step 114 to empty the container from the cleaning water. These two steps 112, 114 are repeated once or twice to thoroughly clean the capillary tube 8 and the container.

Next step 116 in this process is to bring back the capillary tube 8 to its starting position. Thus, the step motor 10 is started again, this time in reversed direction, and keeps on driving the capillary tube 8 upwards until at step 118 it is determined that the upper position is reached. The answer yes at step 118 is obtained when the guiding plate 14 reaches the optical sensor 17. Thereby a first repetition is performed and the process starts from the beginning again to repeatedly measure the fluorescence of new samples under the same conditions and with the same high accuracy.

Thus, the present invention has been described with a preferred embodiment, but is not intended to be limited to this embodiment. A person skilled in the art could readily modify this invention without departing from the scope of the invention. For example changing and rearranging filters and lenses in the optical housing depending on which application is needed lies well within the scope of the invention. Thus, the invention is only limited by the following claims.

We claim:

1. Apparatus for repeatedly and automatically performing fluorometric measurement on different test samples, the samples incorporating a fluorescent tag capable of emitting fluorescent radiation, the apparatus comprising an excitation radiation source including an incandescent filament, an optical unit for providing light of an appropriate wavelength for excitation of the fluorescent tag contained within the test sample and for collecting the emitted fluorescent radiation without disturbances from the excited wavelength, the optical unit comprising an L-shaped light channel, the excitation radiation source cooperating with the optical unit, an electronic unit for controlling the intensity of the incandescent filament of the excitation radiation source and evaluating the emitted fluorescent radiation, and a capillary tube movably provided at the center of the intersection between the two legs of the L-shaped light channel and aligned with the incandescent filament, the capillary tube being moveable between two positions and being repeatedly, between each measurement, suppliable with a new test sample.

2. Apparatus according to claim 1, wherein the excitation radiation source and the electronic unit are arranged to form a 90 degree angle in relation to each other, the electronic unit and the excitation radiation source being of a substantially rectangular box shape.

3. Apparatus according to claim 2, wherein a step motor is provided at the top of a space between the electronic unit and the excitation radiation source, and a threaded shaft is provided at the lower end of the step motor and extends towards the bottom of the space between the electronic unit and the excitation radiation source and parallel thereto.

4. Apparatus according to claim 3, wherein securing means are provided at the end of the threaded shaft to which the capillary tube is fixedly secured, the capillary tube extending in the same direction as the threaded shaft and passing through a guiding tube and the optical unit.

5. Apparatus according to claim 3, wherein the threaded shaft is provided with a guiding plate which is movable in a guiding track provided on top of the electronic unit to ensure that the threaded shaft and the capillary tube are always maintained in parallel with the electronic unit and the excitation radiation source.

6. Apparatus according to claim 4, wherein the securing means are provided with two nipples which are used as connections for two hoses, one of which nipples leads to a suction device for drawing the test sample into the capillary tube and the other of which nipples leads to a water supply used to flush and clean the capillary tube.

7. Apparatus according to claim 1, wherein the optical unit is arranged between the electronic unit and the excitation radiation source, the top surface of the optical unit being perpendicular to both the electronic unit and the excitation radiation source.

8. Apparatus according to claim 5, wherein an optical sensor is provided at an upper end of the guiding track.

9. Apparatus according to claim 1, wherein the excitation radiation source is provided with a lamp holder in which a lamp comprising the incandescent filament is arranged in alignment with the capillary tube by means of an adjusting element.

10. Apparatus according to claim 1, wherein the excitation radiation source is provided with a light channel comprising a condenser lens and an IR filter.

11. Apparatus according to claim 1, wherein an excitation filter for filtering out a wavelength that will excite the fluorescent tag is provided in the L-shaped light channel of the optical unit.

12. Apparatus according to claim 1, wherein aspherical lenses, a mirror for reflecting the emitted light and an emission filter for filtering out the emitted light and for preventing the excited light from passing are provided in the L-shaped light channel.

13. Apparatus according to claim 12, wherein the optical unit is provided with an additional light channel and a beam divider for dividing light into the additional light channel.

14. Apparatus according to claim 13, wherein a diode is provided at the end of each of the light channels.

15. Apparatus according to claim 9, wherein the electronic unit is provided with a light regulator for keeping the intensity of the lamp constant.

16. Apparatus according to claim 14, wherein the electronic unit is further provided with an integrator circuitry connected to one of the diodes for measuring the emitted fluorescent radiation.

17. Apparatus according to claim 16, wherein the integrator circuitry is connected to an analog/digital converter, which in turn is connected to a computer for evaluation of the measurement obtained by the diode and the integrator circuitry.

18. Apparatus according to claim 4, wherein the threaded shaft is provided with a guiding plate which is movable in a guiding track provided on top of the electronic unit to ensure that the threaded shaft and the capillary tube are always maintained in parallel with the electronic unit and the excitation radiation source.

19. Method for repeatedly and automatically performing fluorometric measurement on different test samples, the samples incorporating a fluorescent tag capable of emitting fluorescent radiation, the method comprising the following steps:

(a) verifying that a container containing the test sample is in place, (b) moving a capillary tube downwards until it is immersed into a test sample, (c) filling the capillary tube with the test sample, (d) subjecting the test sample to light from an excitation radiation source, (e) measuring light emitted from the test sample, (f) emptying the container and the capillary tube of the test sample, (g) supplying water to flush and clean the capillary tube and the container, (h) emptying the container and the capillary tube of the water, (i) returning the capillary tube to the starting position, and (j) repeating steps (a) through (i).

* * * * *